US010711298B2

(12) United States Patent
Roehl et al.

(10) Patent No.: US 10,711,298 B2
(45) Date of Patent: Jul. 14, 2020

(54) OLIGONUCLEOTIDE DETECTION METHOD

(75) Inventors: Ingo Roehl, Memmelsdorf (DE);
Markus Schuster, Bayreuth (DE);
Stephan Seiffert, Kulmbach (CH)

(73) Assignee: AXOLABS GMBH, Kulmbach (DE)

( * ) Notice: Subject to any disclaimer, the term of this patent is extended or adjusted under 35 U.S.C. 154(b) by 239 days.

(21) Appl. No.: 13/124,411

(22) PCT Filed: Oct. 6, 2009

(86) PCT No.: PCT/EP2009/062926
§ 371 (c)(1),
(2), (4) Date: Apr. 15, 2011

(87) PCT Pub. No.: WO2010/043512
PCT Pub. Date: Apr. 22, 2010

(65) Prior Publication Data
US 2011/0201006 A1 Aug. 18, 2011

(30) Foreign Application Priority Data

Oct. 15, 2008 (EP) .................... 08166721

(51) Int. Cl.
*C12Q 1/68* (2018.01)
*C12Q 1/6816* (2018.01)
*C07H 21/04* (2006.01)
(52) U.S. Cl.
CPC ................. *C12Q 1/6816* (2013.01)
(58) Field of Classification Search
None
See application file for complete search history.

(56) References Cited

U.S. PATENT DOCUMENTS

| 5,298,392 | A | * | 3/1994 | Atlas et al. | ................... | 435/6.14 |
| 5,539,082 | A | * | 7/1996 | Nielsen et al. | ............... | 530/300 |
| 6,403,313 | B1 | * | 6/2002 | Daksis et al. | ................ | 435/6.12 |
| 6,444,650 | B1 | * | 9/2002 | Cech | ................ | C12Y 207/0704 514/44 A |
| 6,444,661 | B1 | * | 9/2002 | Barton | .................. | C07F 15/008 514/185 |
| 6,811,977 | B2 | * | 11/2004 | Wold et al. | ..................... | 435/6.1 |
| 2006/0014191 | A1 | * | 1/2006 | Lao | .......................... | B82Y 5/00 435/6.14 |
| 2006/0094032 | A1 | * | 5/2006 | Fougerolles | ....... | A61K 31/7088 435/6.16 |
| 2007/0248578 | A1 | * | 10/2007 | Tcherepanova | ........ | A61K 39/00 424/93.21 |
| 2008/0064113 | A1 | * | 3/2008 | Goix | .................. | G01N 35/1095 436/86 |
| 2008/0200566 | A1 | * | 8/2008 | Verdin | ..................... | C12Q 1/42 514/789 |

OTHER PUBLICATIONS

How Many Species of Bacteria Are There? wideGeek.co, accessed Sep. 23, 2011.*
"Virrus," Wikipedia.com, accessed Apr. 18, 2012.*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
"List of sequenced bacterial genomes" (Wikipedia.com; accessed Jan. 24, 2014).*
"Pathological lying," Wikipedia.com (accessed Jun. 1, 2017), four pages.*
"Human Genome Project" (Wikipedia.com, accessed Jun. 7, 2013).*
Rossi, S. et al., Identification of PCR-Amplified Genetically Modified Organisms (GMOs) DNA by Peptide Nucleic Acid (PNA) Probes in Anion-Exchange Chromatographic Analysis; Journal of Agricultural and Food Chemistry (2007) 55, 2509-2516.
Lesignoli, F. et al., Recognition and Strand Displacement of DNA Oligonucleotides by Peptide Nucleic Acid High-performance Ion-exchange Chromatographic Analysis; Journal of Chromatography A, 922 (2001) 177-185.
Mardirossian, G. et al., In Vivo Hybridization of Technetium-99m-Labeled Peptide Nucleic Acid (PNA); Journal of Nuclear Medicine: Official Publication, Society of Nuclear Medicine, vol. 38, No. 6, Jun. 1997, pp. 907-913.
Kiyosawa, J. et al., Disclosing Hidden Transcripts: Mouse Natural Sense-Antisense Transcripts Tend to be Poly(a) Negative and Nuclear Localized; Genome Research, Cold Spring Harbor Laboratory Press, Woodbury, NY, US, vol. 15, No. 4, Apr. 1, 2005, pp. 463-474.
International Search Report, application No. PCT/EP2009/062926, dated Jan. 18, 2010.
Totsingan et al, "Label-free selective DNA detection with high mismatch recognition by PNA beacons and ion exchange HPLC," Organic & Biomolecular Chemistry vol. 6, 2008, pp. 1232-1237.
Lesignoli, Francesca, et al.: "Recognition and Strand Displacement of DNA Oligonucleotides by Peptide Nucleic Acids (PNAs) High Performance Ion-Exchange Chromatographic Analysis," Journal of Chromatography A, vol. 922, pp. 177-185, 2001.
Xi, Chuanwu, et al.: "Use of DNA and Peptide Nucleic Acid Molecular Beacons for Detection and Quantification of rRNA in Solution and in Whole Cells," Applied and Environmental Microbiology, vol. 69(9), pp. 5673-5678, 2003.
Arora et al., "Bioavailability and Efficacy of Antisense Morpholino Oligomers Targeted to c-myc and Cytochrome . . . " Journal of Pharmacetical Sciences 91:1009-1018 (2002).
Lin et al., "Application of LC-MS for quantitative analysis and metabolite identification . . . " Journal of Pharmaceutical and Biomedical Analysis 44:330-341 (2007).

* cited by examiner

*Primary Examiner* — Bradley L. Sisson
(74) *Attorney, Agent, or Firm* — Medler Ferro Woodhouse & Mills PLLC

(57) ABSTRACT

The invention relates to a method for the detection of oligonucleotides using anion exchange high performance liquid chromatography. Fluorescently labelled peptide nucleic acid oligomers, complementary to the oligonucleotide are hybridized to the oligonucleotides. Anion exchange high performance liquid chromatography is then performed and the hybridized moieties detected and quantitated. The invention also relates to a method for the simultaneous detection of both strands of an oligonucleotide in parallel from one sample, and a kit for use in qualitative and quantitative detection of one or two strands of an oligonucleotide.

12 Claims, 9 Drawing Sheets

Specification includes a Sequence Listing.

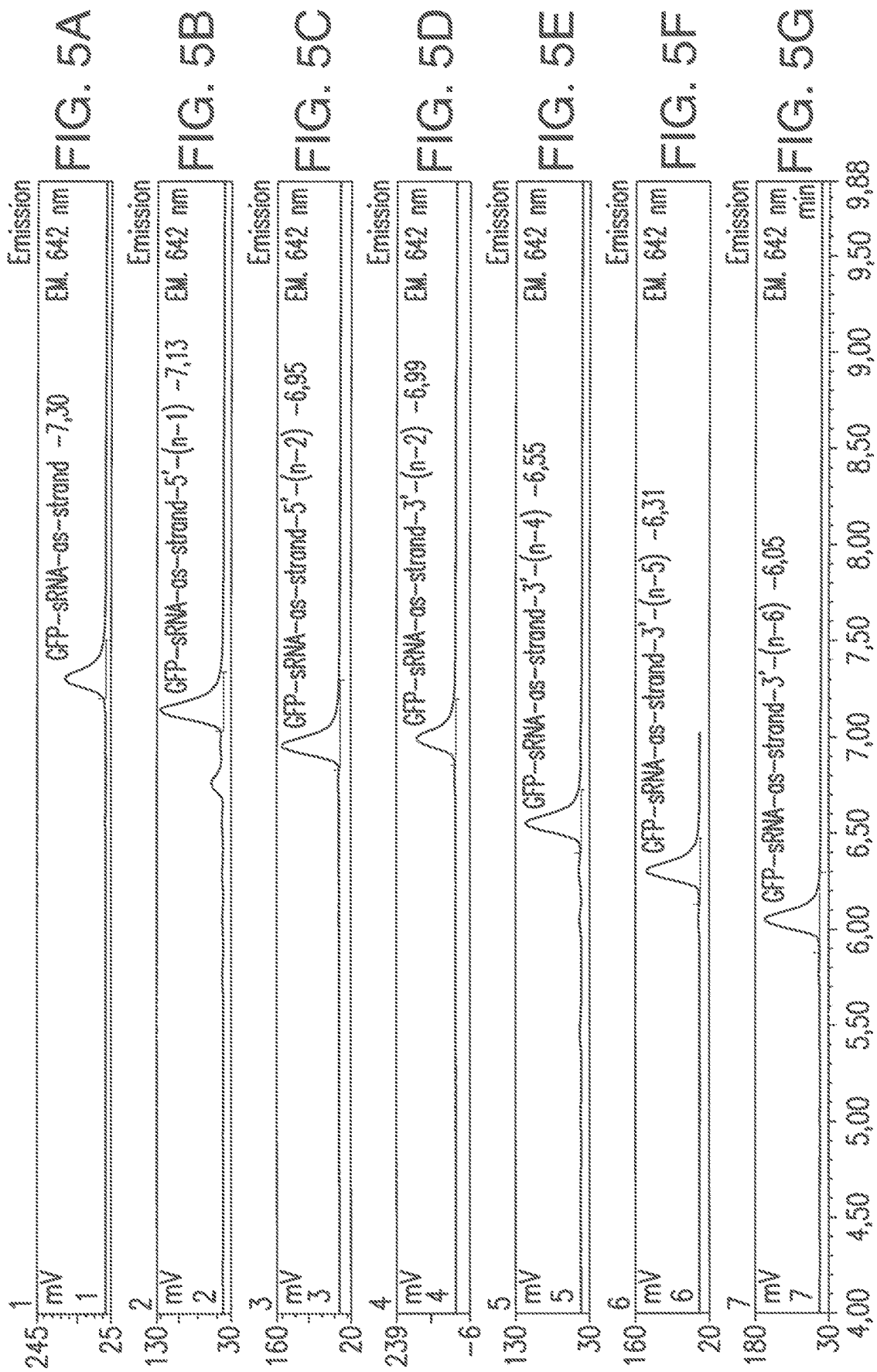

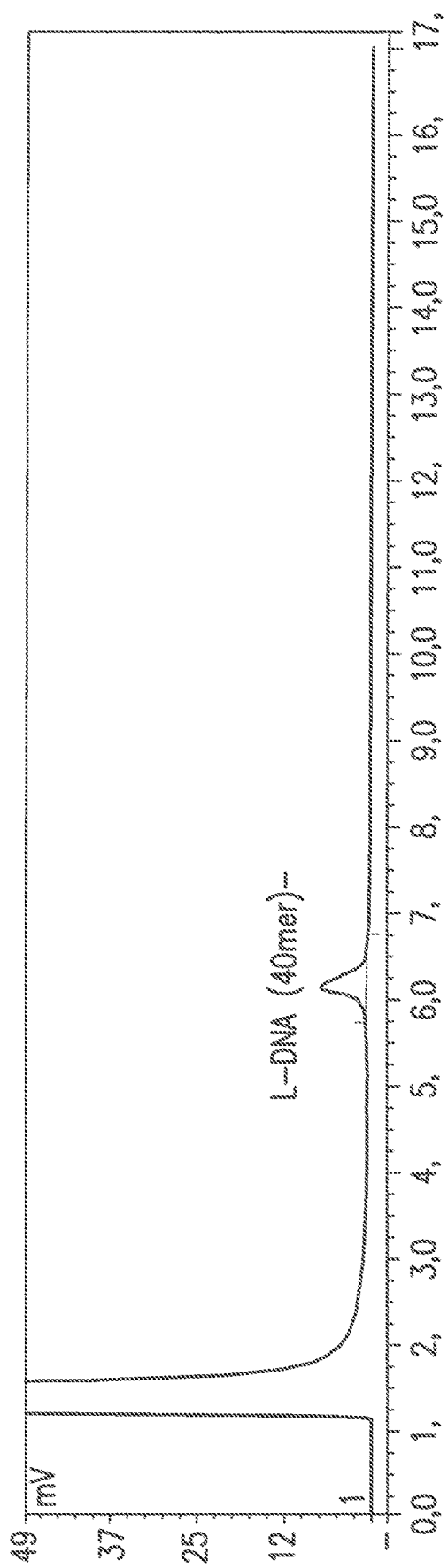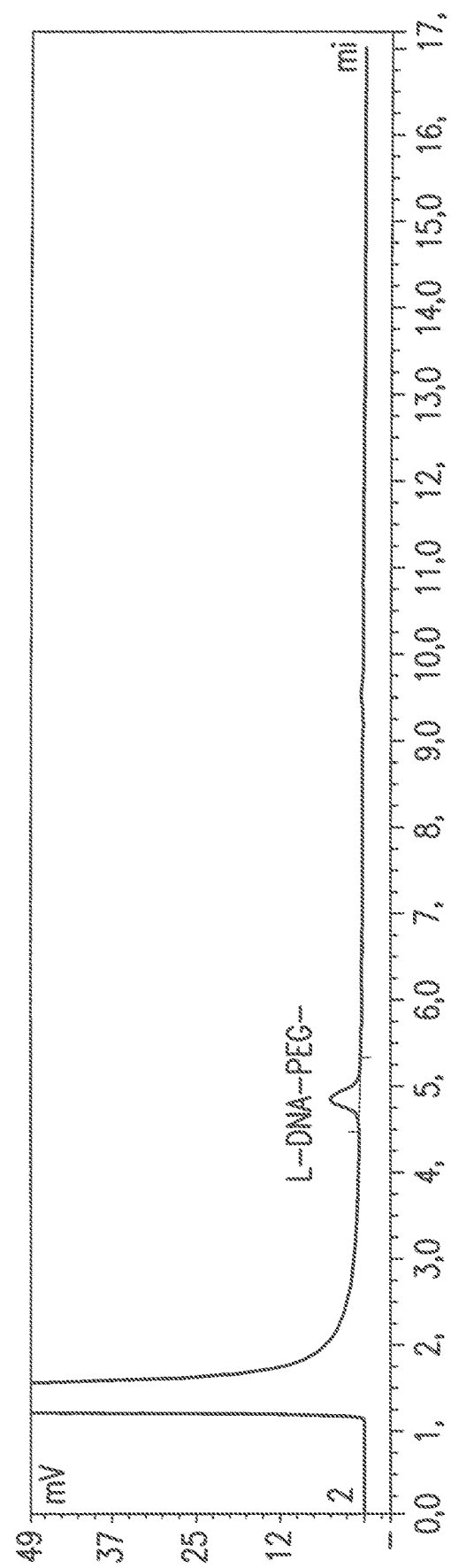

OLIGONUCLEOTIDE DETECTION METHOD

The instant application contains a Sequence Listing which has been submitted in ASCII format via EFS-Web and is hereby incorporated by reference in its entirety. Said ASCII copy, created on Apr. 14, 2011, is named 25305.txt and is 7,095 bytes in size.

The present invention relates to a new simplified method for the detection of oligonucleotides, including RNA, DNA and mixed oligonucleotides, antisense oligonucleotides, short interfering RNA (siRNA), microRNAs (miRNAs), aptamers and also spiegelmers. In addition, the present invention relates to a method for the simultaneous detection of both strands of a double stranded oligonucleotide in a single measurement, e.g. for siRNA.

Oligonucleotides of known sequences are commonly used in a wide variety of chemical and biological applications, and have also gained high importance in the diagnosis and treatment of diseases. In particular, antisense oligonucleotides, short interfering RNA (siRNA) and aptamers are promising pharmalogical tools and therapeutic agents. The qualitative and quantitative detection of these oligonucleotides in samples like cells, tissue, blood or plasma is a prerequisite to assess their therapeutic use and to monitor their stability in vivo.

Different methods for the detection of oligonucleotides are cited in the literature and disclosed in published patent applications, e.g. WO/2008/046645. Most established procedures for quantitative and qualitative detection of oligonucleotides are based on hybridisation with complementary oligonucleotides via Watson-Crick base pairing. Peptide nucleic acids (PNAs) are oligonucleotide mimics in which the sugar-backbone is replaced by a pseudopeptide chain of N-aminoethylglycine monomers. They are often used in probe-based oligonucleotide detection methods as they bind to complementary DNA or RNA sequences with high affinity, specificity and stability (U.S. Pat. No. 6,395,474). WO/2008/046645 mentions the use of PNA probes in a RT-PCR-based oligonucleotide detection assay. U.S. Pat. No. 6,045,995 describes the qualitative and quantitative detection of oligonucleotides by capillary gel electrophoresis. Rossi et al describe the identification of PCR-amplified oligonucleotides by PNA probes in anion-exchange high performance liquid chromatography (HPLC) (J. Agric. Food Chem. 2007, 55, 2509-2516).

However most of the existing assays to determine oligonucleotides in biological samples are not able to detect metabolites or to separate metabolites signals from the signal generated by the intact oligonucleotide. For example in PCR-based methods signals are usually generated of the intact drug only or as the sum of various metabolites together with the intact drug. Capillary gel electrophoresis with fluorescence detection leads to quantitative separation of intact oligonucleotide from its metabolites, but this methodology needs extraction and desalting steps during sample preparation. In addition, recoveries of the analyte molecules are variable and an internal standard is needed for normalization. Another major limitation of the currently used oligonucleotide detection methods is that only one of the two strands can be detected in one measurement, which is particularly disadvantageous for oligonucleotide duplex determination (e.g. siRNA).

Thus it would be of great advantage to have a reproducible and quick method for oligonucleotide detection in samples which is capable of analysing oligonucleotides and its metabolites in a sample. Moreover, in view of the rising importance of siRNA and its derivatives in therapy and diagnostics, there is a need for a reproducible and quick method capable of detecting both strands of the oligonucleotide and its metabolites in one measurement.

Disclosed is a method for qualitative and quantitative detection of an oligonucleotide comprising the steps of selecting a sample containing or suspected of containing said oligonucleotide, forming a hybridization mixture by contacting the sample with a fluorescently labeled peptide nucleic acid (PNA) probe which is fully complementary to at least 10 or more nucleotides of said oligonucleotide, separating hybridized moieties formed between said oligonucleotide and said PNA probe from unhybridized moieties by anion exchange high performance liquid chromatography (aIEX-HPLC), and qualitatively and/or quantitatively detecting said hybridized moieties by fluorescence spectroscopy. A major advantage of the present invention over other oligonucleotide detection methods is the simple sample preparation prior to detection, e.g. no clean-up procedures, amplification or extraction steps are required. Therefore any variability regarding the recovery of the analyte is avoided. In preferred embodiments the sample is treated with Proteinase K in a buffer containing SDS, followed by precipitation of the SDS with a saturated KCl solution. Thereby degradation of the oligonucleotides in the sample is efficiently prevented.

Excess non-hybridized PNA-probe elutes in the void volume of the HPLC and no interfering signals during the gradient separation are expected from the probe. Therefore a high excess of the PNA-probe can be used to kinetically control the hybridization process without establishing a step to extract the excess probe from the sample. The use of the PNA probe also eliminates the complete background fluorescence from the biological matrix, as it elutes with the void volume of the aIEX-HPLC. Also signals generated from unspecific hybridization of the PNA-probe with RNA or DNA coming from the biological matrix is eluted separately in the washing step of the HPLC gradient. Therefore only analyte specific signals can be detected during HPLC gradient with high selectivity. Hence the aIEX-HPLX setup works very robust even if loaded with high biological background.

Due to the uncharged backbone of the PNA it shows high affinity to the corresponding oligonucleotide strand (no electrostatic repulsion as for DNA/DNA, DNA/RNA and RNA/RNA duplexes) which leads to a thermodynamically controlled hybridization even in presence of a competing RNA strand as in the case of siRNA duplexes. Another major improvement of this method over other methods is the capability to detect metabolites and to separate metabolite signals from the signal generated by the intact oligonucleotide. The higher separation power for the metabolites is another result of the uncharged backbone of the PNA-probe. Elution depends strongly on the metabolite length, the shorter the metabolite, the earlier it elutes from the HPLC column within the gradient. Also a 5'-phosphorylated oligonucleotide can be separated from the non-phosphorylated identical sequence of the same length. As the 5'-phosphorylation only occurs after the delivery of the siRNA into the cell this can be used to distinguish extracellular from intracellular delivered siRNA in tissues. Then the intracellular 5'-phosphorylated siRNA can serve as a marker for the amount of active drug in tissue compared to the overall amount of drug delivered into the organ.

Sensitivity and reproducibility of the herein described oligonucleotide detection method: For a model sequence (RD-1003) the lower limit of quantitation (LLOQ) in plasma is about 250 amol of the oligonucleotide with the stock calibration approach. The assay works with high reproducibility (variation<5%).

The major advantages of the present invention over other published HPLC-based oligonucleotide quantitation methods are the quick and simple sample preparation, the lack of amplification steps prior to detection, the high sensitivity and reproducibility, the robustness of the assay, the high-throughput capability and the capability to detect both strands of the oligonucleotide and its metabolites in one measurement. Rossi et al describe the identification of oligonucleotides in anion-exchange HPLC (J. Agric. Food Chem. 2007, 55, 2509-2516). In contrast to the present invention, additional sample preparation steps and amplification of the oligonucleotides by PCR are necessary prior to detection. Further, a simultaneous detection of both strands is impossible, as the hybridisation protocol requires nucleolytic cleavage of one of the strands.

Most of the previously described assays require individual calibration curves due to the variable unspecific background from different tissues or plasma. In contrast, unspecific background signals do not interfere with the assay of the present invention. Hence, in preferred embodiments of the invention, calibration curves generated from a dilution series in buffer can be used for tissue and plasma samples.

In another aspect of the invention methods are provided for qualitative and quantitative detection of both strands of an oligonucleotide duplex in parallel from one sample, comprising the steps of selecting a sample containing or suspected of containing said oligonucleotide; forming a hybridization mixture by contacting the sample with a fluorescently labeled peptide nucleic acid (PNA) probe which is fully complementary to at least 10 or more nucleotides of the sense strand of said oligonucleotide, contacting the hybridization mixture with a second fluorescently labeled PNA probe, which is fully complementary to at least 10 or more nucleotides of the antisense strand of said oligonucleotide, separating hybridized moieties formed between said oligonucleotide strands and said PNA probes from unhybridized moieties by aIEX-HPLC, qualitatively and/or quantitatively detecting said hybridized moieties by fluorescence spectroscopy. This is the first procedure that allows detection of both strands of an oligonucleotide duplex in parallel from one sample.

In the most preferred embodiment two fluorescently labeled PNA-probes are used for the detection of oligonucleotide duplexes. Each probe hybridizes specifically to either the sense or antisense strand of the oligonucleotide. In one embodiment, the same fluorescence label is used for detection of both strands. The duplex is designed of two strands with different length or the two probes are thus designed that hybridization leads to different retention times of the two single strands in the aIEX-HPLC analysis. In another embodiment, two different fluorescence labels are used for detection of both strands with two fluorescence detectors in one HPLC setup.

This opens new possibilities not only for quantification from biological samples but also for CMC characterization of oligonucleotide duplexes, e.g to directly characterize the ratio of the two single strands in a siRNA duplex as the ratio of peak areas for the individual strands. The signal intensity only depends on the fluorescence signal after the hybridization procedure and is independent from the single strand specific UV extinction coefficients.

In a preferred embodiment, a known concentration of the oligonucleotide that should be detected is added to the unknown sample, and is also added to the calibration and blank sample. This so-called stock calibration approach improves the sensitivity of the assay as detailed in the example section.

In another preferred embodiment the sample is plasma, in yet another preferred embodiment the sample is tissue.

In another preferred embodiment, the method is used for quantitative and qualitative detection of siRNA and derivatives. In yet another embodiment the method can be used for the quantitative and qualitative detection of the in vivo metabolism of therapeutic or diagnostic siRNA.

In one embodiment said siRNA is detected from in vitro cell cultures that have been transfected with said siRNA In one embodiment the method is used for quantitative and qualitative detection of microRNA and derivatives. Preferably said microRNAs are detected from tissue lysates.

In another embodiment the method is used for quantitative and qualitative detection of aptamers. Preferably, said aptamers are spiegelmers with L-ribose (L-RNA) or L-deoxyribose (L-DNA). In one embodiment, said aptamer is pegylated.

In yet another embodiment the method can be used to distinguish extracellular from intracellular delivered siRNA in tissues.

A number of dyes have been described for fluorescently labeling oligonucleotides. Preferred fluorescence labels include Atto 610, Atto 425 and Atto 520, but any other fluorescence labels known to a person skilled in the art can be used in the method.

In yet another embodiment, this invention is directed to kits suitable for performing an assay which detects the presence, absence or number of one or two strands of an oligonucleotide and its metabolites in a sample. The kits of this invention comprise a ready-to-use plate preparation comprising one or more PNA probes and all other reagents or compositions necessary to perform the assay. The use of the kit simplifies the performance of the assay and improves the reproducibility of the assay. Preferred kits of the invention make use of a fully automated robotic system for oligonucleotide detection, where all reagents are added by a pipetting robot. Thus the reproducibility of the assay is further improved. In addition, this setup can be used for high-throughput analysis of oligonucleotides in different samples. In one preferred embodiment, the kits comprise a 96 well-plate preparation, in yet another embodiment the kits comprise a 384 well plate preparation.

For convenience, the meaning of certain terms and phrases used in the specifications, examples and claims are provided below. If there is an apparent discrepancy between the usage of a term in other parts of this specification and its definition provided in this section, the definition provided in this section shall prevail.

The term "oligonucleotide" as used herein refers to an oligomer or polymer of either ribonucleic acid (RNA) or deoxyribonucleic acid (DNA), as well as non-naturally occurring oligonucleotides. Non-naturally occurring oligonucleotides are oligomers or polymers which contain nucleobase sequences which do not occur in nature, or species which contain functional equivalents of naturally occurring nucleobases, sugars, or inter-sugar linkages, like aptamers, spiegelmers, peptide nucleid acids (PNA), threose nucleic acids (TNA), locked nucleic acids (LNA), or glycerol nucleic acids (GNA). This term includes oligomers that contain the naturally occurring nucleic acid nucleobases adenine (A), guanine (G), thymine (T), cytosine (C) and uracil (U), as well as oligomers that contain base analogs or modified nucleobases. Therefore the person skilled in the art understands that the term "oligonucleotide" comprises but is not limited to RNA, DNA and mixed oligonucleotides, antisense oligonucleotides, short interfering RNA (siRNA), microRNAs (miRNAs), aptamers and also spiegelmers.

Oligonucleotides can derive from a variety of natural sources such as viral, bacterial and eukaryotic DNAs and RNAs. Other oligonucleotides can be derived from synthetic sources, and include any of the multiple oligonucleotides that are being manufactured for use as research reagents, diagnostic agents or potential and definite therapeutic agents. The term includes oligomers comprising of a single strand nucleic acid or a double strand nucleic acid. The two strands of a double strand nucleic acid are defined as "sense strand" and "antisense strand".

As used herein, the term "strand comprising a sequence" refers to an oligonucleotide comprising a chain of nucleotides that is described by the sequence referred to using the standard nucleotide nomenclature. However, as detailed herein, such a "strand comprising a sequence" may also comprise modifications, like modified nucleotides. As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. "Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein.

The term "hybridized moieties" refers to any oligonucleotide or any of its metabolites which are hybridized to the PNA probe whereas "unhybridized moieties" refer to any oligonucleotide or any of its metabolites which are not hybridized to the PNA probe. The term "siRNA" refers to a double stranded RNA molecule that is capable of blocking gene expression in a highly conserved regulatory mechanism known as RNA interference (RNAi).

Hence the term "therapeutic siRNA" refers to a double stranded RNA molecule used as a compound to treat, prevent or manage disorders and diseases of a subject by blocking expression of specific disease or disorder related genes. Preferably, such subject is a mammal, most preferably a human patient.

The term "oligonucleotide metabolite" includes oligonucleotides from which 1 or more nucleotides are deleted from the 3' and/or the 5' end. The term "oligonucleotide metabolite" further includes any naturally or synthetically modified oligonucleotide, for example oligonucleotides comprising phosphorylated 3' or 5' ends.

Also claimed are the methods and kits as hereinbefore described, especially with reference to the examples below. The following examples, references, sequence listing and figures are provided to aid the understanding of the present invention, the true scope of which is set forth in the appended claims. It is understood that modifications can be made in the procedures set forth without departing from the spirit of the invention.

SHORT DESCRIPTION OF THE FIGURES

FIG. 5A-5G shows separation of drug metabolites.

FIG. 7A-7B shows a chromatogram for detection of spiegelmer in lung tissue.

EXAMPLES

Example 1: Detection of GFP-siRNA by PNA-Probe HPLC

This material and method section describes the assay procedure how to determine a GFP-siRNA from biological samples. Additionally this procedure can be also used with small variations for all other oligonucleotides that can form Watson-crick base pairs. The procedure allows the determination of only one strand in the case of single- and double stranded oligonucleotides and the quantification of both strands in parallel from double stranded oligonucleotides, e.g. siRNA. The dye-probe is an fluorescently labeled PNA (Peptide Nucleic Acid) strand that is fully complementary to at least 10 or more nucleotides of the oligonucleotide that should be quantified (complementary is defined as perfect Watson-Crick base pairing).

Plasma, serum or tissue samples are shipped on dry ice and stored at −80° C. until used. Prior to the analysis plasma samples are thawed on ice and processed by a proteinase K treatment in Epicentre Cell and Tissue Lysis Solution at 65° C. for 25 min. For the proteinase K treatment 30 μA plasma are mixed with 30 μA Epicentre Cell and Tissue Lysis Solution, 4 μA proteinase K solution and 36 μl H$_2$O to a final volume of 100 μl.

Tissues samples are pulverized in frozen state and up to 100 mg frozen powder were suspended in 1 mL Epicentre Cell and Tissue Lysis Solution, treated with an ultrasonic stick and subsequently lysed with a proteinase K treatment at 65° C. All proteinase K treated samples are further diluted with Epicentre Cell and Tissue Lysis Solution before employed in the HPLC sample preparation step.

After the proteinase K treatment 20 μl of a 3M KCl solution is added to 200 l of the plasma or tissue samples to precipitate the SDS. Subsequently the samples are centrifuged for 15 min and the supernatant is further used for siRNA determination.

For hybridization, 100 μl of the diluted supernatant containing between 0.5 and 250 fmol siRNA, is mixed in 96-PCR well plates with 5 μl of a 1 μM Atto610-PNA-probe solution targeting the antisense strand. Hybridization buffer is added to a final volume of 200 μl (to 190 μl if the sense strand of the siRNA duplex should be detected also). The plate is sealed and incubated at 95° C. for 15 min in a PCR instrument.

The temperature of the PCR instrument is lowered to 50° C. If the sense strand of the siRNA duplex should be detected 10 µl of a 1 µM Atto425-PNA-probe (or of the Atto610-PNA-probe) targeting the sense strand is added to each well for a final volume of 200 µl. After shaking for additional 15 min at 50° C. are cooled to room temperature and the samples are put into the HPLC autosampler.

Figure 3:
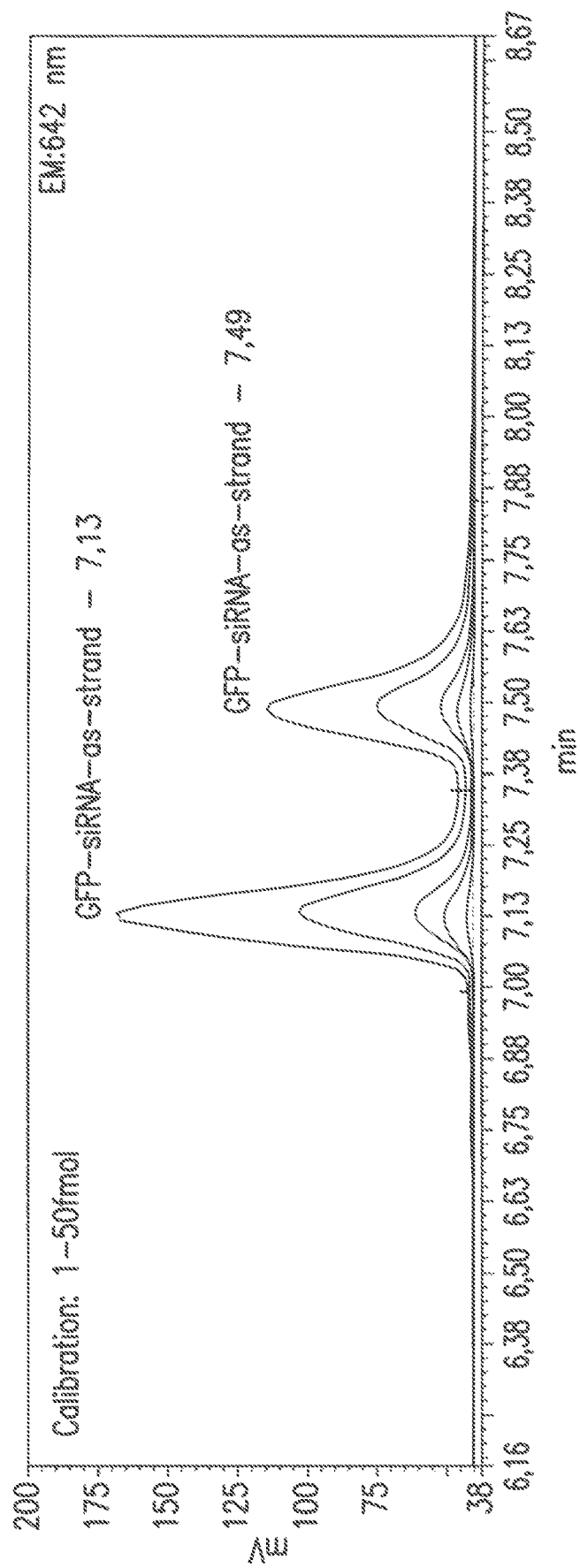
FIG. 3 shows calibration curves for the simultaneous analysis of both strands using two PNA probes with the same dye.

Calibration curves are generated from a siRNA dilution series under identical conditions. A representative chromatogram of the calibration curve used in the analysis of both strands of an oligonucleotide is provided in FIG. 3.

TABLE 1

Sequences of PNA-Probes used for detection of a siRNA targeting GFP

GFP-siRNA probe set

| | |
|---|---|
| 5'-Atto425-(OO)-TCG TGC TGC TTC ATG-3' | Seq.Id. No. 1 Sense |
| 5'-Atto610-(OO)-TCG TGC TGC TTC ATG-3' | Seq.Id. No. 2 Sense |
| 5'-Atto610-(OO)-ACA TGA AGC AGC ACG-3' | Seq.Id. No. 3 Antisense |

HPLC Analysis with Fluorescence Detection of the Probe/Antisense Strand Duplex

100 µl of each hybridized sample (½) are injected into the HPLC system connected to a Dionex RF2000 fluorescence detector. For detection of both siRNA strands with the two different fluorescence dyes a second Dionex RF2000 fluorescence detector is used connected in a row after the first detector. The chromatography is conducted at 50° C. under native conditions with NaClO$_4$ as eluent salt on a Dionex DNA Pac PA100 column.

Figure 1:
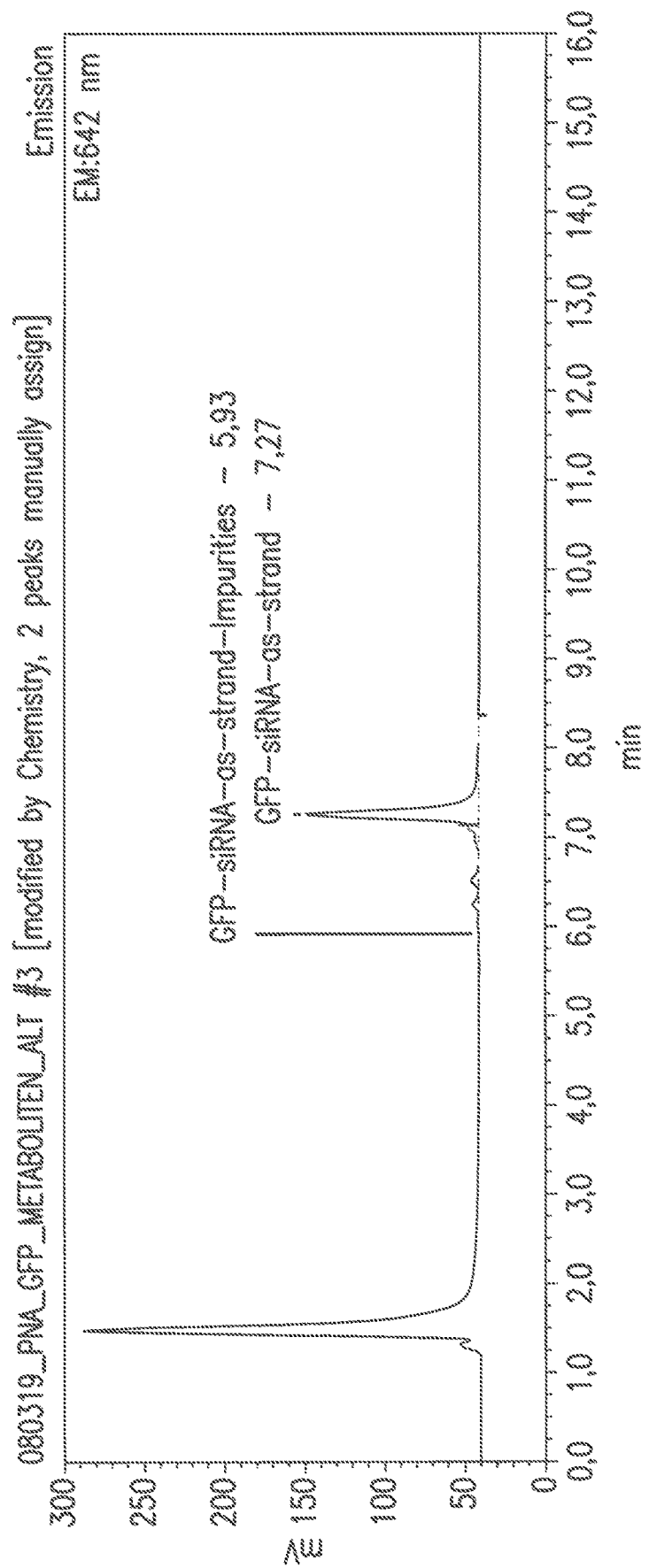
FIG. 1 shows a chromatogram for the detection of one strand of the siRNA.
Figure 2:
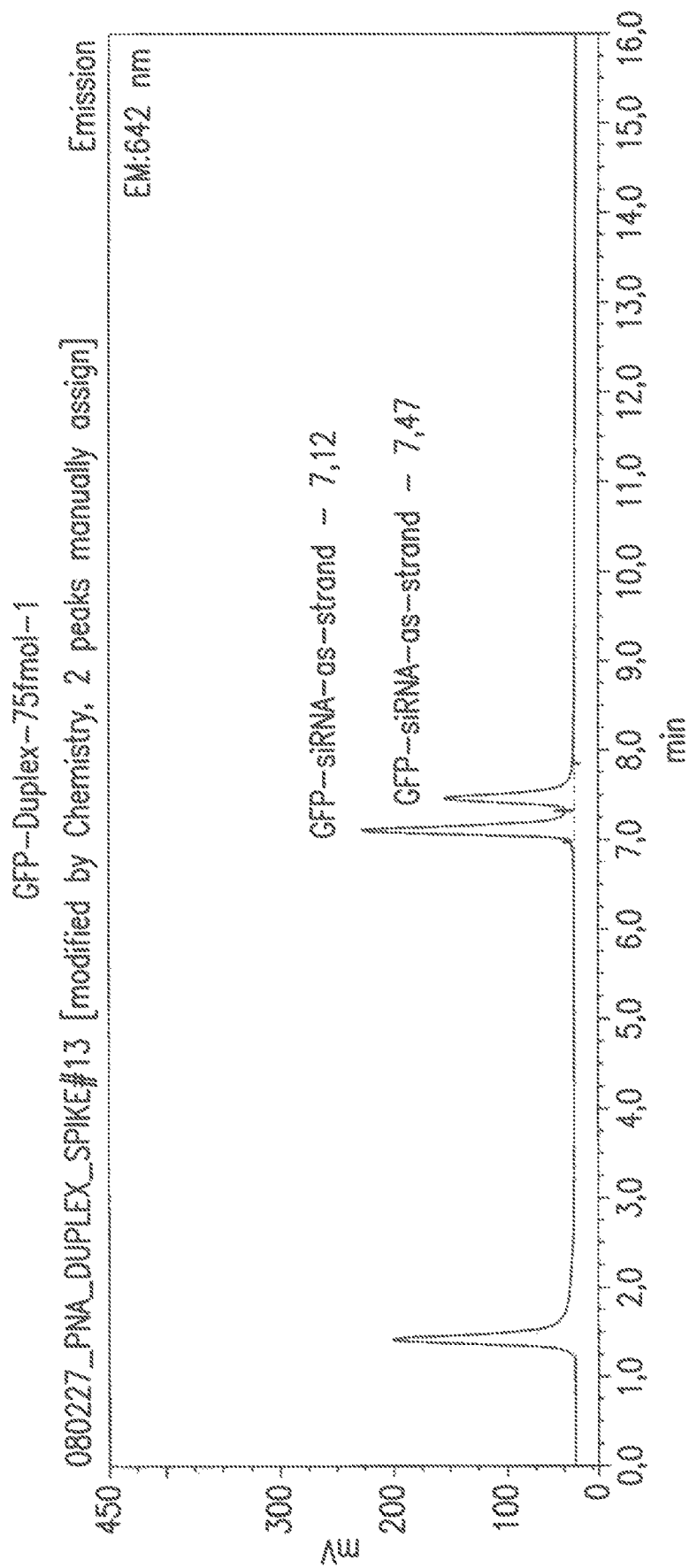
FIG. 2 shows a simultaneous analysis of both strands using two PNA probes with the same dye.
Figure 4A:
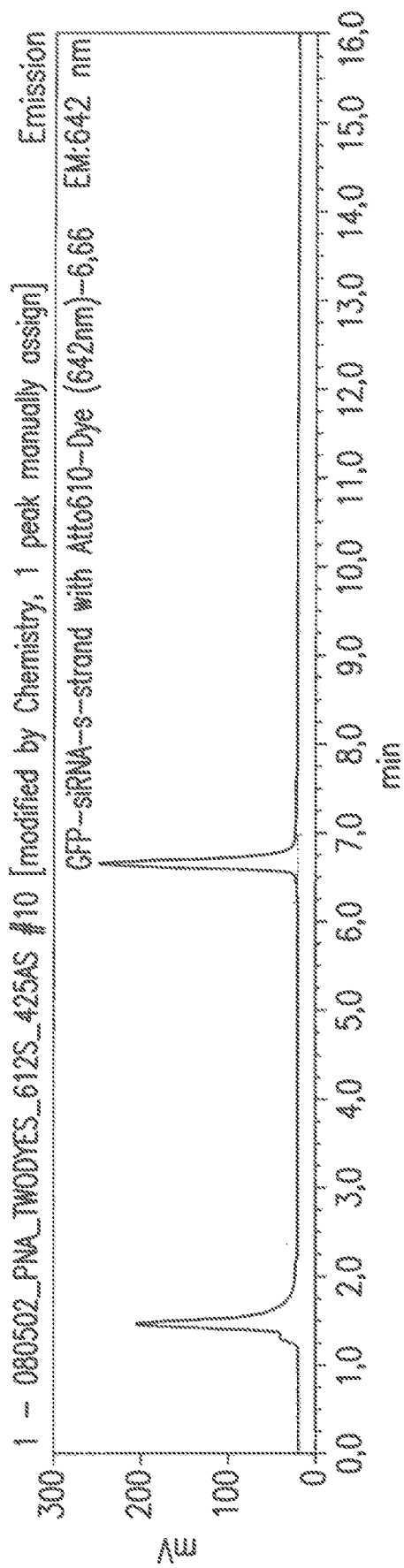
FIG. 4A-4B shows simultaneous analysis of both strands using two PNA probes with different fluorescence labels, detection with two fluorescence detectors.
Figure 4B:
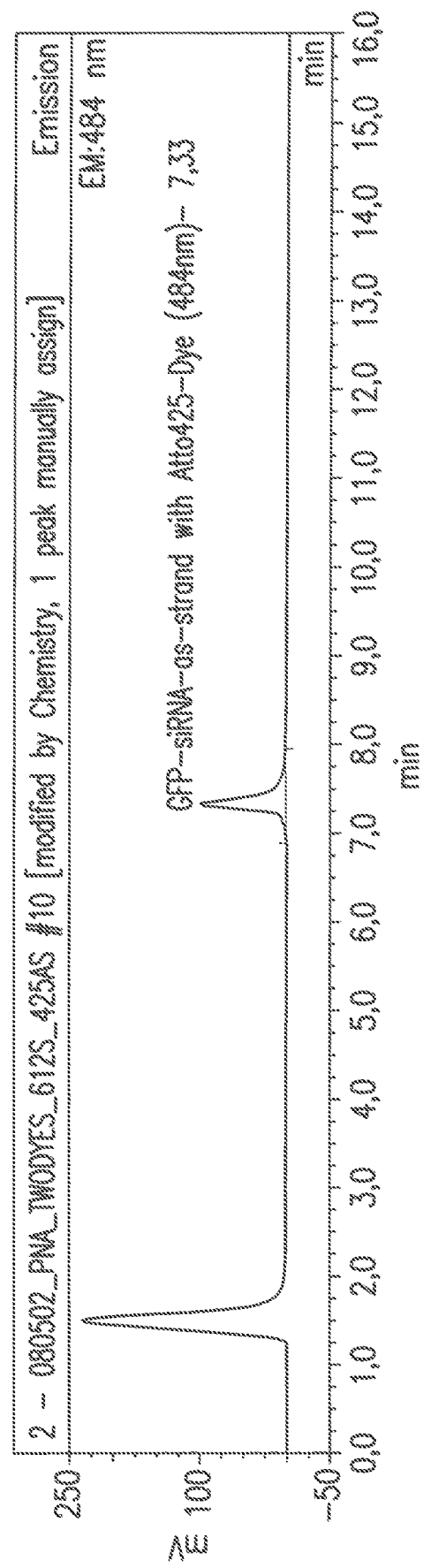

A typical chromatogram for the detection of one strand is shown in FIG. 1, a typical chromatogram for the simultaneous analysis of both strands using two PNA probes with the same dye is provided in FIG. 2. A representative chromatogram of the calibration curve used in the analysis of both strands of an oligonucleotide is provided in FIG. 3. In FIG. 4 a typical chromatogram of the simultaneous analysis of both strands using two PNA probes with different fluorescence labels and their detection with two fluorescence detectors is shown.

HPLC-Conditions:
Column: Dionex DNAPac PA100 (4×250 mm analytical column)
Temp.: 50° C.
Flow: 1 ml/min
Injection: 100µ
Detection: Excitation: 612 nm; Emission: 642 nm (first detector)
Excitation: 436 nm; Emission: 484 nm (second detector if needed)

TABLE 2

HPLC Gradient Table

| Time | % A | % B |
|---|---|---|
| −1.00 min | 91 | 9 |
| 1.00 min | 91 | 9 |
| 9.0 min | 80 | 20 |

TABLE 2-continued

HPLC Gradient Table

| Time | % A | % B |
|---|---|---|
| 9.5 min | 0 | 100 |
| 12.5 min | 0 | 100 |
| 13.0 min | 91 | 9 |
| 16.0 min | 91 | 9 |

The concentrations of the GFP-siRNA in plasma and tissue samples are determined using ion-exchange HPLC to separate the analytes and quantify the area under the peak with fluorescence detection. Under the native IEX-HPLC conditions used, interfering matrix compounds as well as excess of the fluorescence labeled probes elute in the void volume of the column. Non-specific signals from hybridization of the fluorescence labeled probes with matrix RNA/DNA are shifted to higher retention times allowing for good resolution of signal with little co-eluting background. The specific signals generated by the duplexes consisting of fluorescent labeled probes and the corresponding intact siRNA strand typically elutes between 5 to 7 min.

Quantitation is performed based on an external calibration curve generated from a standard siRNA dilution series (from 0.5 to 250 fmol siRNA) which is hybridized and analyzed as described above. The linear range of this assay is from 0.5 to 250 fmol siRNA on the column with an LLOQ of ~0.6 ng siRNA in 1 mL plasma and ~5 ng siRNA in tissue.

Reagents:
50 µM Standard GFP-siRNA stock solution (in house prep)
Hybridization Buffer: 50 mM TRIS-Cl; 10% ACN (in house prep.)
Proteinase K (20 mg/ml): Peqlab No. 04-1075; Lot: 11024
Lysis buffer: Epicentre Cell and tissue lysis solution (# MTC096H)
MilliQ-water: 18.2 MΩ
PNA-Probes: see Table 1
KCl: 3M solution in H$_2$O (in house prep)
HPLC-System A for fluorescence detection:
HPLC Eluent A: 25 mM TRIS-HCl; 1 mM EDTA; 50% ACN; pH=8
HPLC Eluent B: 800 mM NaClO$_4$ in A
Material:
Ultrasonic stick, Bandelin Sonoplus (Berlin), HD 2070 MS72 with UW 2070
1.5 ml Eppendorf tubes
Eppendorf twin.tec PCR plate 96 (#951020389)
Eppendorf Mastercycler gradient
Ultra Clear cap-Stripes, Peqlab (#82-0866-A)
Dionex Ultimate 3000 HPLC: Solvent Rack
Dual Pump Ultimate 3000
Autosampler Ultimate 3000
Column Oven Ultimate 3000 with 10 port switch valve
UV-Detector VWD 3000
Fluorescence-Detector RF2000

Alternatively, the following HPLC conditions were used for the detection of oligonucleotides, especially for detection of miRNAs and siRNAs:
Column: Dionex DNA Pac PA100 (250×4 mm)
Temperature: 50° C.
Eluent A: 10 mM Sodiumphosphate; 100 mM NaCl; 5% ACN
Eluent B: 10 mM Sodiumphosphate; 1M NaCl; 5% ACN
Eluent C: 90% ACN

TABLE 3

HPLC Gradient Table - alternative protocol (Standard conditions for detection of miRNAs and siRNAs)

| Time [min] | Flow [mL/min] | Eluent A [%] | Eluent B [%] | Eluent C [%] |
|---|---|---|---|---|
| 0.00 | 1.00 | 40 | 20 | 37 |
| 1.00 | 1.00 | 40 | 20 | 37 |
| 10.00 | 1.00 | 8 | 55 | 37 |
| 10.50 | 1.00 | 0 | 90 | 10 |
| 13.50 | 1.00 | 0 | 90 | 10 |
| 14.00 | 1.00 | 40 | 20 | 37 |
| 17.00 | 1.00 | 40 | 20 | 37 |

Example 2: Automated 96-Well Plate Preparation

This section describes a new sample preparation protocol making use of microtiter plates. Therein, manual handling steps are reduced to a minimum to improve the reproducibility of the assay. All components of the mixture including hybridization buffer, dye-probe and the siRNA spike are added by a pipetting robot to a 96-well plate. Also the preceding SDS precipitation of the samples can be performed in a microtiter plated based setup.

With his procedure it is possible to prepare 96-well plates on stock for a defined oligonucleotide, wherein only the sample solution has to be added. Accordingly, this ready-to-use preparation works like a kit and can be used for quick high-throughput analysis of samples containing or suspected of containing defined oligonucleotides.

Plate Preparation

In a 96 well microtiter plate the wells form a rectangular grid of 8 rows (labeled A through H) and 12 columns (labeled 1 through 12). For an automated 96 well plate preparation, a mastermix is prepared manually according to table 4 and 100 μl are added to each well of the plate by a pipetting robot. To wells in row 1-10, 50 μl water is added. Row 1-9 serve for sample analysis, row 10 serves as control for the 1 fmol spike and rows 1-12 for the calibration curves. To wells 11-12, 50 μl medium and 50 μl of a siRNA dilution are added. The siRNA dilutions are prepared by the pipetting robot starting with a 100 nM siRNA solution and are listed below. This 96-well plate is further referred to as "prepared plate".

TABLE 4

Mastermix for plate preparation

| substance | per vial | Mastermix (=×500) |
|---|---|---|
| Water | 31 μl | 15500 μl |
| PNA Probe 1 pmol/μl | 5 μl | 2500 μl |
| 1 fmol-siRNA-Spike: 0.5 fmol/μl | 4 μl | 2000 μl |
| Acetonitril | 20 μl | 10000 μl |
| 1M Tris pH 8.0 | 40 μl | 20000 μl | siRNA Dilutions for Calibration Curves
20 nM (500 fmol)
10 nM (250 fmol)
4 nM (100 fmol)
2 nM (50 fmol)
1 nM (25 fmol)
0.4 nM (10 fmol)
0.2 nM (5 fmol)
0.1 nM (2.5 fmol)
0.02 nM (0.5 fmol)
0.01 nM (0.25 fmol)

Addition of Samples to Prepared Plate/SDS Precipitation Step

100 μl aliquots of samples are pipetted to wells into all rows (A-H) of columns 1 to 9 of a precooled 96 well microtiter plate, and to these wells 10 μl 3M KCl are added by a pipetting robot. After 15 minutes of centrifugation at 3800 U/min and 4° C., 50 μl of the supernatant are transferred by the pipetting robot to the according columns of a prepared plate.

For the control, lysis buffer or medium is precipitated with 3M KCl and 50 μl of the supernatant added to column 10-12 of the prepared plate. 100 μl of each well are injected onto aIEX-HPLC.

Example 3: Separation of Drug Metabolites

For separation of different drug metabolites purified 3' end (3' n-2, 3' n-4, 3' n-5, 3' n-6) and 5' end (5' n-1, 5'n-2, 5'n-3) metabolites of the as strand of GFP-siRNA, from which 1 to 6 nucleotides were deleted from the 3' or 5' end, respectively, were analysed according to the assay procedure described in Example 1. Metabolites are given in table 5, a typical chromatogram for separation of metabolites is given in FIG. 5.

TABLE 5

Representative metabolites of GFP-siRNA
GFP-siRNA

| Name | Sequence | Seq.Id |
|---|---|---|
| *Sense* | | |
| GFP-siRNA-s-strand | 5'-CCACAUGAAGCAGCACGACUU-3' | 4 |
| *Antisense* | | |
| GFP-siRNA-as-strand | 5'-AAGUCGUGCUGCUUCAUGUGGUC-3' | 5 |
| GFP-siRNA-as-strand-5'-(n − 1) | 5'-AGUCGUGCUGCUUCAUGUGGUC-3' | 6 |
| GFP-siRNA-as-strand-5'-(n − 2) | 5'-GUCGUGCUGCUUCAUGUGGUC-3' | 7 |
| GFP-siRNA-as-strand-5'-(n − 3) | 5'-UCGUGCUGCUUCAUGUGGUC-3' | 8 |
| GFP-siRNA-as-strand-3'-(n − 2) | 5'-AAGUCGUGCUGCUUCAUGUGG-3' | 9 |

TABLE 5-continued

Representative metabolites of GFP-siRNA
GFP-siRNA

| Name | Sequence | Seq.Id |
|---|---|---|
| GFP-siRNA-as-strand-3'-(n - 4) | 5'-AAGUCGUGCUGCUUCAUGU-3' | 10 |
| GFP-siRNA-as-strand-3'-(n - 5) | 5'-AAGUCGUGCUGCUUCAUG-3' | 11 |
| GFP-siRNA-as-strand-3'-(n - 6) | 5'-AAGUCGUGCUGCUUCAU-3' | 12 |

Example 4: Detection of miRNA

The assay was used under standard conditions to evaluate the possibility to detect miRNA from tissue lysates. As an example the mouse liver specific miRNA-122 was detected from mouse tissue lysate (positive control), jejunum (negative control) and from lysate spiked with synthetically generated miRNA-122 strands (Lagos-Quintana, et al. Current Biology, Vol. 12, 735-739). From literature it is known, that in liver of mice three different types of miRNA-122 sequences are expressed:

```
miRNA-122a:
5'-UGGAGUGUGACAAUGGUGUUUG-3'   (Seq. ID. No. 13)

miRNA-122b:
5'-UGGAGUGUGACAAUGGUGUUUGU-3'  (Seq. ID. No. 14)

miRNA-122c:
5'-UGGAGUGUGACAAUGGUGUUUGA-3'  (Seq. ID. No. 15)
```

All synthetic standards were synthesized as 5'-OH and as 5'-Phosphate sequence. As the three species showed small variations at the 3'-end the PNA-Probe was designed in way that it fully matches with all three miRNA-122 sequences, starting at the third base of the 5'-end of the miRNA-122 with 17 bases in length:

```
PNA-Probe:
                              (Seq. ID. No. 16)
5'-Atto425-OO-AACACCATTGTCACACT-3'
```

Figure 6A:
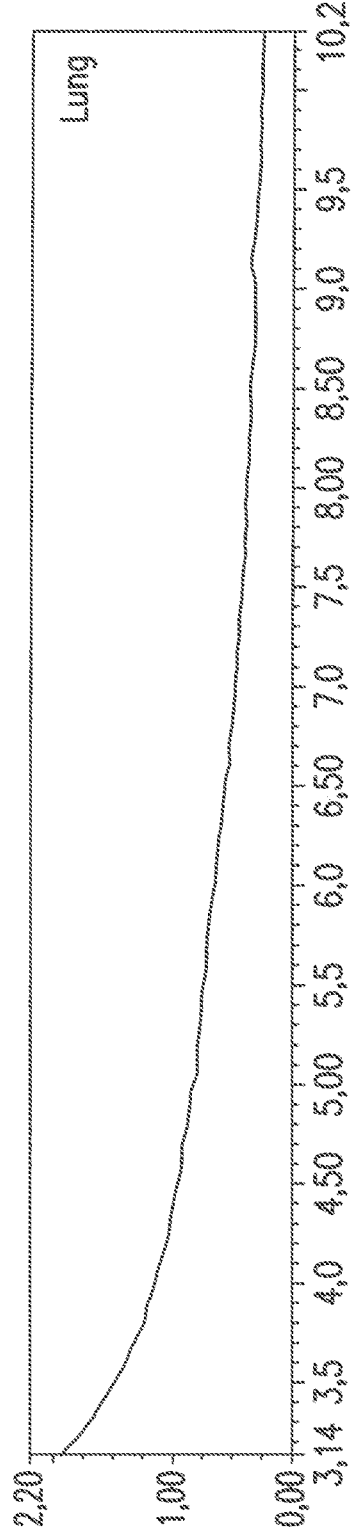
FIG. 6A-6C shows a chromatogram for the detection of miRNAs.
Figure 6B:
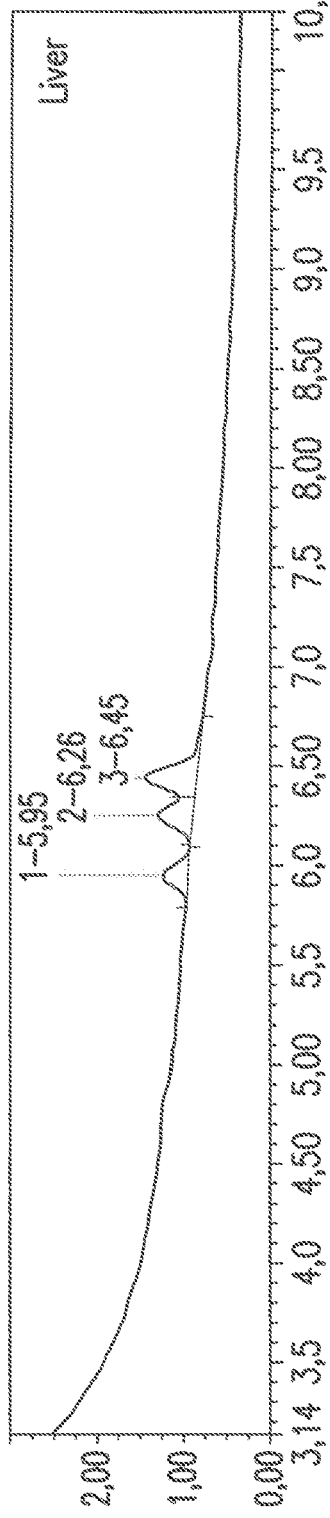
Figure 6C:
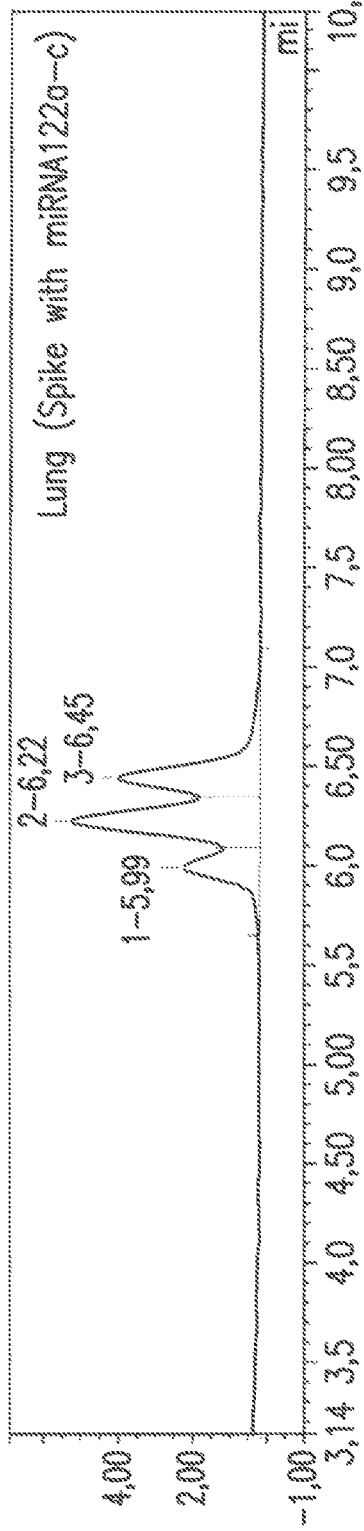

HPLC was performer with the conditions as described in the alternative protocol detailed in example 1 and shown in table 3. HPLC-traces generated from mouse lung lysate (miRNA122 negative tissue) spiked with synthetically generated miRNA-122 showed three separated peaks. The retention time of this peaks fully match with signals, that were found in lysates from liver (1 mg liver injected). The quantitation of the total peak area and calculation of the total miRNA-122 concentration in liver lead to approximately ~35 ng/g. The miRNA-122 negative control from jejunum or lung tissue samples showed no signal for miRNA-122 as expected (FIG. 6).

Example 5: Detection of Spiegelmer-DNA (L-DNA) with and without Pegylation

Spiegelmers are aptamer molecules with non-natural L-ribose (L-RNA) or L-deoxyribose (L-DNA) sugar backbone that show no Watson-Crick base pair interaction with the natural D-oligonucleotides. As PNA is a non-chiral mimic of oligonucleotides with Watson-Crick base pair properties it was expected, that the PNA-probes can also be used to detect this non-natural oligonucleotide species. To increase the circulation half life of spiegelmers or aptamers this molecules are often pegylated with branched 40 kDa PEG, that usually hampers the analysis of this complex molecules.

As a proof of concept for the detection of this therapeutically interesting molecule class a pegylated and a non-pegylated version of the following L-DNA sequence were synthesized and analysed with the here described assay after orotrachael administration in mice:

Non-PEG-Spiegelmer:

```
                                  (Seq. ID. No. 17)
(NH2C6)-CCAGCCACCTACTCCACCAGTGCCAGGACTGCTTGAGGGT
```

PEG-Spiegelmer:

```
                                  (Seq. ID. No. 18)
PEG(40kDa)-(NHC6)-CAGCCACCTACTCCACCAGTGCCAGGACTG
CTTGAGGGT
```

The following 17 mer-PNA-Probe was used for hybridization and detection of the spiegelmer from plasma, lung, liver and kidney samples:

```
                              (Seq. ID. No. 19)
5'-Atto425-OO-GTCCTGGCACTGGTGGA-3'
```

Gradient conditions were adjusted to the longer oligonucleotide sequences compared with to the siRNA strands to elute the spiegelmer-PNA-duplex within the gradient of the HPLC method.

The following HPLC conditions were applied:
Column: Dionex DNA Pac PA100 (250×4 mm)
Temperature: 50° C.
Eluent A: 10 mM Sodiumphosphate; 100 mM NaCl; 5% CAN
Eluent B: 10 mM Sodiumphosphate; 1M NaCl; 5% ACN
Eluent C: 90% ACN

TABLE 6

HPLC gradient conditions for pegylated spiegelmer

| Time [min] | Flow [mL/min] | Eluent A [%] | Eluent B [%] | Eluent C [%] |
|---|---|---|---|---|
| 0.00 | 1.00 | 40 | 20 | 40 |
| 1.00 | 1.00 | 40 | 20 | 40 |
| 10.00 | 1.00 | 5 | 55 | 40 |
| 10.50 | 1.00 | 0 | 60 | 40 |
| 13.50 | 1.00 | 0 | 60 | 40 |
| 14.00 | 1.00 | 40 | 20 | 40 |
| 17.00 | 1.00 | 40 | 20 | 40 |

TABLE 7

HPLC gradient conditions for Spiegelmer

| Time [min] | Flow [mL/min] | Eluent A [%] | Eluent B [%] | Eluent C [%] |
|---|---|---|---|---|
| 0.00 | 1.00 | 35 | 25 | 40 |
| 1.00 | 1.00 | 35 | 25 | 40 |
| 10.00 | 1.00 | 0 | 60 | 40 |
| 10.50 | 1.00 | 0 | 60 | 40 |
| 13.50 | 1.00 | 0 | 60 | 40 |
| 14.00 | 1.00 | 35 | 25 | 40 |
| 17.00 | 1.00 | 35 | 25 | 40 |

Sensitivity of the method was a little bit compromised for the pegylated Spiegelmer due to peak broadening induced by the polydisperity of the 40 kDa PEG-moiety. Lower limit of detection was increased to ~1 fmol L-DNA on column. Resolution of shorter impurities was not tested, but expected to be lower compared to the shorter siRNA or miRNA strands.

Sample preparation was done according to the standard protocol. The Spiegelmers could be easily detected by this procedure from plasma and all tissue tested, as a sharp single peaks with nearly no biological background interference as shown in FIG. 7.

Example 6: Detection of siRNA from In Vitro Transfection Experiments

Detection of unlabeled siRNA from in vitro cell culture experiments was limited by the fact of the high sensitivity needed and therefore only approaches with amplification step like PCR were successful for unmodified molecules.

The PNA-HPLC assay sensitivity was in range to measure siRNA from cell culture experiments. An 19 base pair siRNA with 2 nt overhang at the 3'-end of both strands was used for transfection of primary hepatocytes at a 30 nM siRNA concentration. Various versions of this duplex with identical sequences, only differing at their 5'-end of the antisense strand were transfected. After transfection the cells were washed with PBS and then lysed by a proteinase K treatment with a concentration of ~2500 cells per uL lysate.

The cell culture lysate was used for the PNA-HPLC assay procedure and ~50000 cells per HPLC run were injected onto the column after hybridization with the complementary antisense strand PNA-probe. Under this assay conditions the intact as-strand and also the 5'-phosphorylated species of the antisense strand could be detected down to approximately 8000 siRNA copies per cell (data not shown).

Example 7: Use of Internal Standards for Normalization (Higher Accuracy)

To further increase the accuracy of the method, especially when used in a GxP environment it is maybe necessary to implement an internal standard for normalization. As a proof of concept a 21 mer RNA-strand was elongated with 3 up to 8 desoxy-T nucleotides at its 3'-end. This normalization standards, together with the 21 mer and its 5'-phosphorylated species were spiked into plasma and then analysed under standard assay and HPLC conditions (see example 1, especially the alternative protocol for HPLC and table 3) for siRNAs.

All elongated standards eluted fully baseline resolved from the 21 mer as well as from the 5'-phosphorylated 21 mer with higher retention times. Some peak interferences were observed with the 3-dT-nucleotide elongated sequence and the 5'-phosphorylated 21 mer, as some synthesis impurities of the elongated strand co-eluted with the 5'-phosphorylated 21 mer.

Figure 8A:
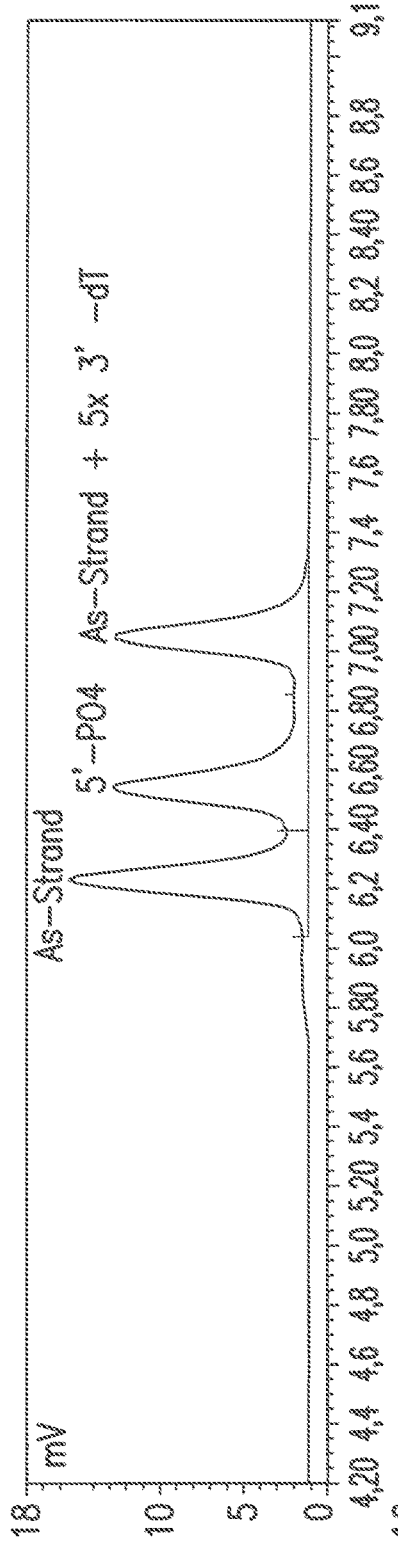
FIG. 8A-8C shows retention time shift by 3'-elongated as-strand sequences.
Figure 8B:
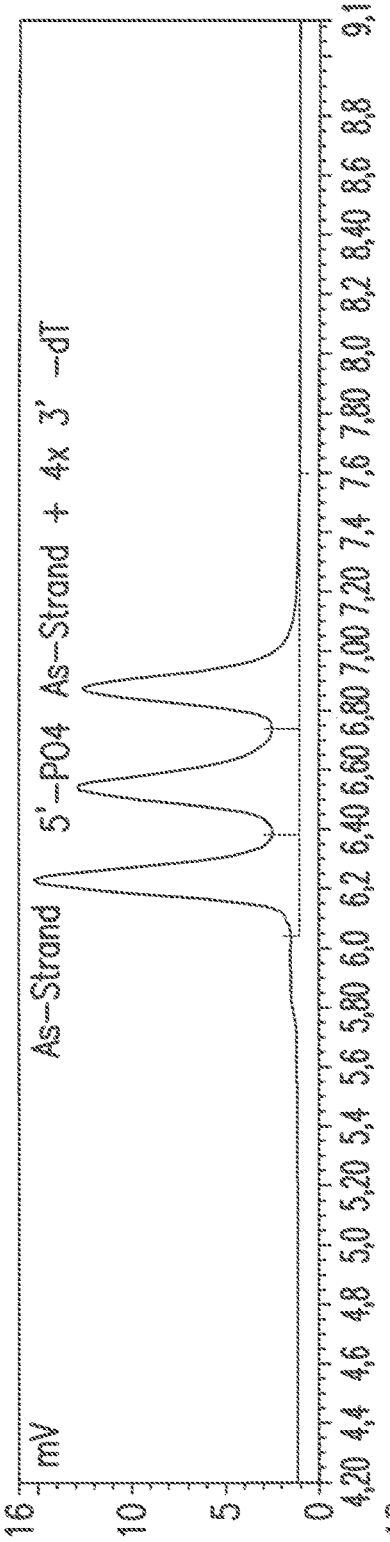
Figure 8C:
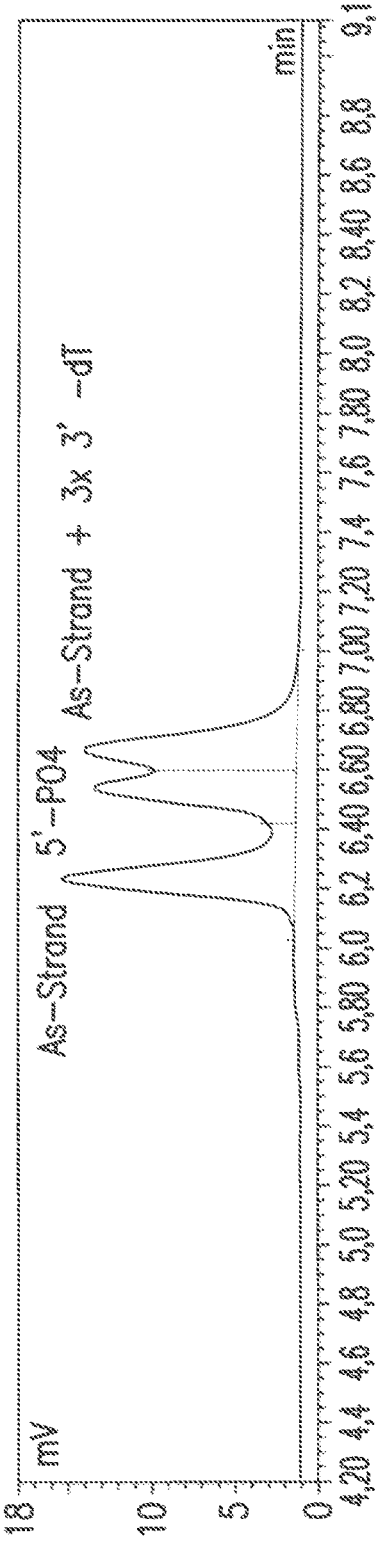

The example shown here is a chromatogram overlay of samples containing the as-strand and the 5'-phosphorylated as-strand mixed with the 3'-elongated as-strand with 3, 4 and 5 desoxythymidine nucleotides at its 5'-end (see FIG. 8). The following sequences were used for the example chromatograms (Letters in capitals represent RNA nucleotides, lower case letters "c", "g", "a" and "u" represent 2' O-methyl-modified nucleotides, "s" represents phosphorothioate and "dT" deoxythymidine):

```
as-strand:
                                (Seq. ID. No. 20)
5'-UCGAAGuACUcAGCGuAAGdTsdT-3' as-strand-5'-PO₄:
                                (Seq. ID. No. 21)
5'-pUCGAAGuACUcAGCGuAAGdTsdT-3' as-strand-(dT)ₙ:
                                (Seq. ID. No. 22,
                                 Seq. ID. No. 23,
                                 Seq. ID. No. 24)
5'-UCGAAGuACUcAGCGuAAGdTdT-(dT)ₙ-3'
with n = 3, 4, 5

PNA-Probe:
                                (Seq. ID. No. 25)
5'-Atto425-OO-CTT ACG CTG AGT ACT TC-3'
```

TABLE 8

Peak resolution calculated according to the USP

| Sequence | Retention Time [min] | Resolution to 5'-PO4 (USP) |
|---|---|---|
| as-strand | 6.23 | 1.70 |
| as-strand - 5'-PO4 | 6.54 | — |
| as-strand + 3x 3'-dT | 6.68 | <1 |
| as-strand + 4x 3'-dT | 6.88 | 2.25 |
| as-strand + 5x 3'-dT | 7.04 | 2.75 |

With this experiment it was also proven, that under standard miRNA and siRNA assay conditions baseline resolution can be achieved for oligonucleotides up to 29 mers, that differ only by one nucleotide in length.

Example 8: Increase of Assay Sensitivity in Tissues

Figure 9A:
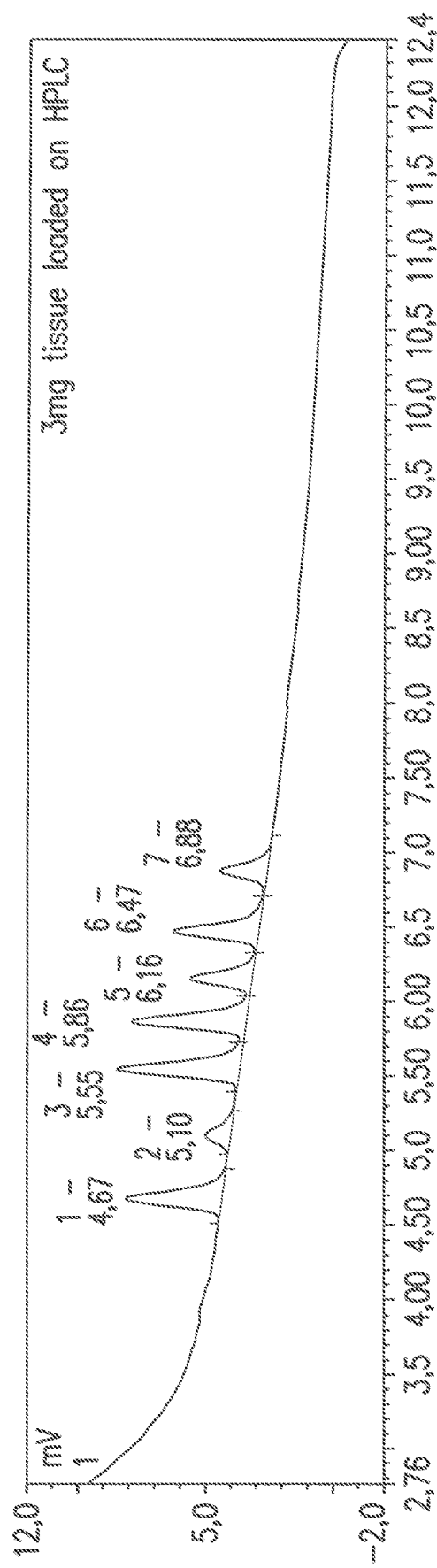
FIG. 9A-9B shows increase in sensitivity by higher tissue loading.
Figure 9B:
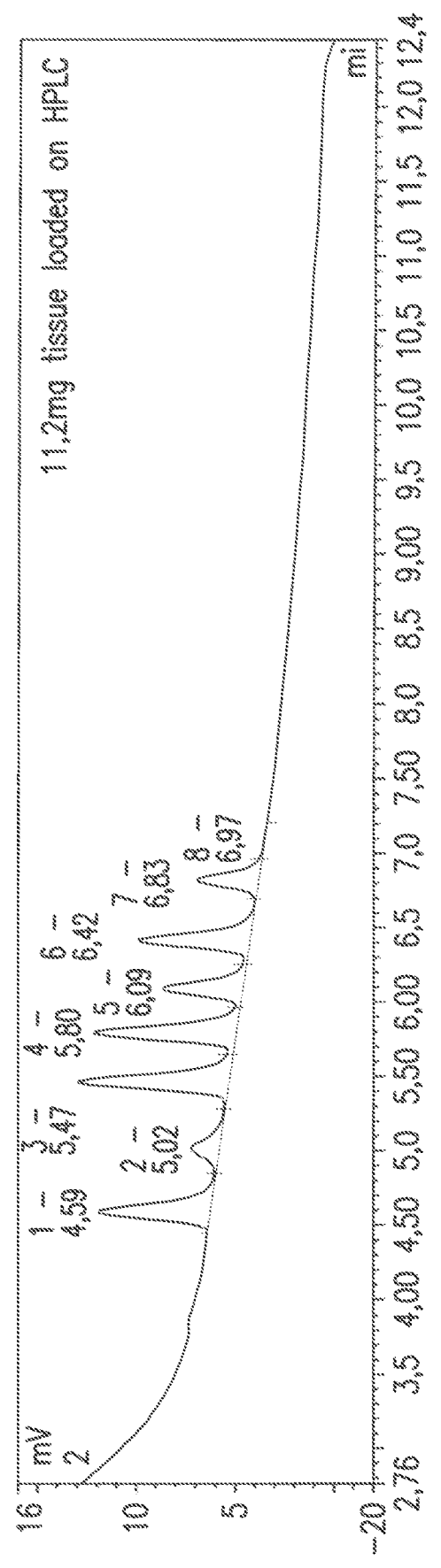

The sensitivity of the assay as described above was restricted to ~2 ng siRNA per g tissue. This limitation was given by the fact that the maximal loaded tissue amount on the column was 2-3 mg per injection, as the baseline noise increased at higher tissue loadings. Switching from the Atto610 dye to the Atto425 dye allows much higher column loadings up to 11 mg without loss of signal sensitivity and chromatographic resolution power. The absolute amount of siRNA at the LOD is still 250 amol oligonucleotide on column. This lead to a lower limit of detection in respect to siRNA tissue concentration of ~400 pg/g (FIG. 9).

In table 9 below a comparison between two chromatographic runs of the same tissue sample, but two separate tissue preparations is shown. In the upper chromatogram 3 mg liver was loaded onto the HPLC column, in the lower chromatogram 11.2 mg was loaded.

Although the results were generated from two different tissue lysate, the calculated tissue siRNA and metabolite concentrations show only minor variation:

TABLE 9

Signal/Noise-Values of identical tissue sample; different tissue amounts loaded on HPLC column

| Peak No. | 3 mg Tissue loaded on HPLC | | | 11 mg Tissue loaded on HPLC | | | Tissue Conc. Delta [ng/g] |
|---|---|---|---|---|---|---|---|
| | Ret. Time min | Tissue Conc. ng/g | S/N | Ret. Time min | Tissue Conc. ng/g | S/N | |
| 1 | 4.67 | 17.1 | 67 | 4.59 | 13.5 | 26.8 | 3.5 |
| 2 | 5.10 | 4.8 | 18 | 5.02 | 4.3 | 8.3 | 0.6 |
| 3 | 5.55 | 20.6 | 87 | 5.47 | 17.5 | 22.8 | 3.1 |
| 4 | 5.86 | 19.4 | 81 | 5.80 | 16.3 | 17.9 | 3.0 |
| 5 | 6.16 | 10.4 | 44 | 6.09 | 9.0 | 8.7 | 1.3 |
| 6 | 6.47 | 14.3 | 61 | 6.42 | 12.5 | 15.7 | 1.8 |
| 7 | 6.88 | 7.7 | 33 | 6.83 | 6.8 | 9.8 | 0.9 |

The invention claimed is:

1. A method for detecting a target therapeutic RNA oligonucleotide having a pre-defined sequence and RNA oligonucleotide metabolites of said target therapeutic RNA oligonucleotide, comprising the steps of:
   (a) preparing a sample containing or suspected of containing said target therapeutic RNA oligonucleotide having said pre-defined sequence and said RNA oligonucleotide metabolites of said target therapeutic RNA oligonucleotide, wherein said target therapeutic RNA oligonucleotide has a length of 10 nucleotides up to 29 nucleotides, and wherein said RNA oligonucleotide metabolites are said target therapeutic RNA oligonucleotide from which 1 or more nucleotides have been deleted from the 3'- and/or the 5'-end, and/or said RNA oligonucleotide metabolites are said target therapeutic RNA oligonucleotide comprising phosphorylated 3'- or 5'-ends, and wherein said sample is an extracellular or intracellular sample,
   (b) forming a hybridization mixture by contacting the sample with a fluorescently labeled peptide nucleic acid (PNA) probe,
   (c) hybridizing the PNA probe to said target therapeutic RNA oligonucleotide having said pre-defined sequence and hybridizing the PNA probe to said RNA oligonucleotide metabolites of said target therapeutic RNA oligonucleotide, wherein said PNA probe and said target therapeutic RNA oligonucleotide having said pre-defined sequence are fully complementary over at least 10 nucleotides of said target therapeutic RNA oligonucleotide having the pre-defined sequence,
   (d) separating hybridized moieties formed between said PNA probe and said target therapeutic RNA oligonucleotide having said pre-defined sequence, and hybridized moieties formed between PNA probe and said RNA oligonucleotide metabolites of said target therapeutic RNA oligonucleotide, from unhybridized moieties by anion exchange high performance liquid chromatography (HPLC), wherein signals associated with said hybridized moieties formed between said PNA probe and said RNA oligonucleotide metabolites of said target therapeutic RNA oligonucleotide are separated from a signal associated with hybridized moieties formed between said PNA probe and said target therapeutic RNA oligonucleotide, and
   (e) detecting quantitatively in a single fluorescence spectroscopy measurement said hybridized moieties formed between said PNA probe and said target therapeutic RNA oligonucleotide having said pre-defined sequence and hybridized moieties formed between said PNA probe and said RNA oligonucleotide metabolites of said target therapeutic RNA oligonucleotide.

2. The method according to claim 1 for detecting both strands of a target therapeutic RNA oligonucleotide duplex having a pre-defined sequence and RNA oligonucleotide metabolites of said target therapeutic RNA oligonucleotide in parallel from one sample, comprising the addition of a second fluorescently labeled PNA probe subsequent to step (b) and then performing steps (c) to (e), wherein said first and said second fluorescently labeled PNA probe are designed as such that (i) hybridization leads to different retention times of the two strands of the target therapeutic RNA oligonucleotide duplex and its corresponding RNA oligonucleotide metabolites of said target therapeutic RNA nucleotide duplex, or (ii) two different fluorescence labels are used.

3. The method according to claim 1, wherein said target therapeutic RNA oligonucleotide having said pre-defined sequence is a siRNA, an antisense RNA or a microRNA.

4. The method according to claim 1, wherein a known concentration of a calibration RNA oligonucleotide detectable by said PNA is added to the sample.

5. The method according to claim 1, wherein the PNA probe is labeled with Atto 610, Atto 425 or Atto 520.

6. The method according to claim 1, wherein the sample is a tissue sample, a plasma sample, or an in vitro cell sample.

7. The method of claim 1, further comprising quantifying the amount of the target therapeutic RNA oligonucleotide having said pre-defined sequence and RNA oligonucleotide metabolites of said target therapeutic RNA oligonucleotide by comparing the detected hybridized moieties to a calibration curve generated from a dilution series of the target therapeutic RNA oligonucleotide having said pre-defined sequence and the PNA probe in buffer.

8. The method of claim 1, wherein the sample is a plasma, serum or tissue sample and the preparing in (a) comprises lysing cells in the sample.

9. The method of claim 1, wherein the hybridizing in (c) comprises mixing the target therapeutic RNA oligonucleotide having a pre-defined sequence with the PNA probe and incubating at 95° C. to form the hybridized moieties.

10. The method of claim 1, wherein the preparing in (a) comprises treating the sample with proteinase K.

11. The method of claim 1, wherein the separating in (c) is conducted under native anion exchange HPLC conditions at 50° C. with $NaClO_4$ as an eluent salt.

12. The method of claim 1, wherein the separating in (c) further comprises non-hybridized PNA probe eluting in the void volume of the HPLC.

* * * * *

SEQUENCE LISTING

```
<160> NUMBER OF SEQ ID NOS: 25

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      backbone: peptide nucleic acid

<400> SEQUENCE: 1
tcgtgctgct tcatg                                                       15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      backbone: peptide nucleic acid

<400> SEQUENCE: 2
tcgtgctgct tcatg                                                       15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      backbone: peptide nucleic acid

<400> SEQUENCE: 3
acatgaagca gcacg                                                       15

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      GFP-siRNA-s-strand

<400> SEQUENCE: 4
ccacaugaag cagcacgacu u                                                21

<210> SEQ ID NO 5
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      GFP-siRNA-as-strand

<400> SEQUENCE: 5
aagucgugcu gcuucaugug guc                                                23

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      metabolite of GFP-siRNA-as-strand-5'-(n-1)

<400> SEQUENCE: 6
agucgugcug cuucauguggg uc                                                22

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      metabolite of GFP-siRNA-as-strand-5'-(n-2)

<400> SEQUENCE: 7
gucgugcugc uucauguggu c                                                  21

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      metabolite of GFP-siRNA-as-strand-5'-(n-3)

<400> SEQUENCE: 8
ucgugcugcu ucaugugguc                                                    20

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      metabolite of GFP-siRNA-as-strand-3'-(n-2)

<400> SEQUENCE: 9
aagucgugcu gcuucaugug g                                                  21

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      metabolite of GFP-siRNA-as-strand-3'-(n-4)

<400> SEQUENCE: 10
aagucgugcu gcuucaugu                                                     19

<210> SEQ ID NO 11
<211> LENGTH: 18
<212> TYPE: RNA
<213> ORGANISM: Artificial Sequence
<220> FEATURE:
<223> OTHER INFORMATION: Description of Artificial Sequence: Synthetic
```

-continued

```
      metabolite of GFP-siRNA-as-strand-3'-(n-5)

<400> SEQUENCE: 11
aagucgugcu gcuucaug                                                   18

<210> SEQ ID NO 12
<211> LENGTH: 17
<212> TYPE: RNA
<213> ORGANISM: Artificial Sequence
<220> FEATURE:
<223> OTHER INFORMATION: Description of Artificial Sequence: Synthetic
      metabolite of GFP-siRNA-as-strand-3'-(n-6)

<400> SEQUENCE: 12
aagucgugcu gcuucau                                                    17

<210> SEQ ID NO 13
<211> LENGTH: 22
<212> TYPE: RNA
<213> ORGANISM: Mus musculus

<400> SEQUENCE: 13
uggaguguga caauguguu ug                                               22

<210> SEQ ID NO 14
<211> LENGTH: 23
<212> TYPE: RNA
<213> ORGANISM: Mus musculus

<400> SEQUENCE: 14
uggaguguga caauguguu ugu                                              23

<210> SEQ ID NO 15
<211> LENGTH: 23
<212> TYPE: RNA
<213> ORGANISM: Mus musculus

<400> SEQUENCE: 15
uggaguguga caauguguu uga                                              23

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      backbone: peptide nucleic acid

<400> SEQUENCE: 16
aacaccattg tcacact                                                    17

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      Spiegelmer with L-deoxyribose backbone

<400> SEQUENCE: 17
ccagccacct actccaccag tgccaggact gcttgagggt                           40

<210> SEQ ID NO 18
<211> LENGTH: 39
<212> TYPE: DNA
```

```
<213> ORGANISM: Artificial Sequence
<220> FEATURE:
<223> OTHER INFORMATION: Description of Artificial Sequence: Synthetic
      Spiegelmer with L-deoxyribose backbone

<400> SEQUENCE: 18
cagccaccta ctccaccagt gccaggactg cttgagggt                              39

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      backbone: peptide nucleic acid

<400> SEQUENCE: 19
gtcctggcac tggtgga                                                     17

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      antisense strand of internal standard siRNA
<220> FEATURE:
<223> OTHER INFORMATION: Description of Combined DNA/RNA Molecule:
      Synthetic antisense strand of internal standard siRNA

<400> SEQUENCE: 20
ucgaaguacu cagcguaagt t                                                21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      antisense strand of internal standard siRNA
<220> FEATURE:
<223> OTHER INFORMATION: Description of Combined DNA/RNA Molecule:
      Synthetic antisense strand of internal standard siRNA

<400> SEQUENCE: 21
ucgaaguacu cagcguaagt t                                                21

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      antisense strand of internal standard siRNA
<220> FEATURE:
<223> OTHER INFORMATION: Description of Combined DNA/RNA Molecule:
      Synthetic antisense strand of internal standard siRNA

<400> SEQUENCE: 22
ucgaaguacu cagcguaagt tttt                                             24

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      antisense strand of internal standard siRNA
<220> FEATURE:
```

```
<223> OTHER INFORMATION: Description of Combined DNA/RNA Molecule:
      Synthetic antisense strand of internal standard siRNA

<400> SEQUENCE: 23
ucgaaguacu cagcguaagt ttttt                                          25

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      antisense strand of internal standard siRNA
<220> FEATURE:
<223> OTHER INFORMATION: Description of Combined DNA/RNA Molecule:
      Synthetic antisense strand of internal standard siRNA

<400> SEQUENCE: 24
ucgaaguacu cagcguaagt tttttt                                         26

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      backbone: peptide nucleic acid
<220> FEATURE:
<223> OTHER INFORMATION: Description of Combined DNA/RNA Molecule:
      Synthetic backbone: peptide nucleic acid

<400> SEQUENCE: 25
cttacgctga gtacttc                                                   17
```